United States Patent
Moses et al.

(10) Patent No.: US 7,840,366 B1
(45) Date of Patent: Nov. 23, 2010

(54) CALIBRATION MANAGEMENT FOR VOLATILE ORGANIC COMPOUND DETECTOR

(75) Inventors: Rex Moses, Nassau Bay, TX (US); Kevin Moses, League City, TX (US); Bradley O'Keefe, Houston, TX (US)

(73) Assignee: Environmental Analytics, Inc., Nassau Bay, TX (US)

( * ) Notice: Subject to any disclaimer, the term of this patent is extended or adjusted under 35 U.S.C. 154(b) by 111 days.

(21) Appl. No.: 12/032,499

(22) Filed: Feb. 15, 2008

Related U.S. Application Data (60) Provisional application No. 60/890,396, filed on Feb. 16, 2007.

(51) Int. Cl.
*G01D 18/00* (2006.01)
(52) U.S. Cl. .............. 702/85; 702/23; 702/182
(58) Field of Classification Search .......... 702/85, 702/22–24, 104, 137, 119, 182–183, 187; 95/1–3, 8; 96/18, 19; 73/1.01, 1.02, 1.06, 73/23.31, 23.21, 23.2; 204/194, 400, 401, 204/431, 228.1, 228.6, 229.8; 324/601–603; 340/501, 502, 517, 531, 605, 632, 634; 431/13–16, 431/22, 24, 26
See application file for complete search history.

(56) References Cited

U.S. PATENT DOCUMENTS

| | | | | |
|---|---|---|---|---|
| H572 H | * | 2/1989 | Hansen | 356/439 |
| 5,206,818 A | | 4/1993 | Speranza | |
| 5,356,594 A | * | 10/1994 | Neel et al. | 422/54 |
| 6,478,849 B1 | * | 11/2002 | Taylor et al. | 95/11 |
| 6,545,278 B1 | * | 4/2003 | Mottier et al. | 250/339.13 |
| 6,672,129 B1 | * | 1/2004 | Frederickson et al. | 73/1.06 |
| 6,722,185 B2 | | 4/2004 | Lawson et al. | |
| 7,017,386 B2 | * | 3/2006 | Liu et al. | 73/1.03 |
| 7,136,904 B2 | | 11/2006 | Bartek et al. | |
| 7,369,945 B2 | | 5/2008 | Miller et al. | |
| 2003/0012696 A1 | * | 1/2003 | Millancourt | 422/83 |
| 2003/0081214 A1 | * | 5/2003 | Mestha et al. | 356/402 |
| 2004/0226345 A1 | * | 11/2004 | McCoy et al. | 73/40.7 |
| 2004/0258213 A1 | * | 12/2004 | Beamon et al. | 379/9 |
| 2005/0000981 A1 | * | 1/2005 | Peng et al. | 222/3 |

(Continued)

OTHER PUBLICATIONS

*Environmental Analytics, Inc. v. TMX2, Inc. and LDAR Solutions, Ltd.*; Case 4:08-cv-03353; USDC, Southern District of Texas; First Amended Complaint; Dec. 10, 2008.

(Continued)

*Primary Examiner*—Mohamed Charioui
*Assistant Examiner*—Ricky Ngon
(74) *Attorney, Agent, or Firm*—Pramudji Law Group PLLC; Ari Pramudji (57) ABSTRACT

A method for calibrating a volatile organic compound (VOC) detector. In one implementation, an initiation request may be received indicating a gas concentration level amount to be used for calibrating a VOC detector. A gas may be provided to the VOC detector according to the gas concentration level amount. The VOC detector may be provided with the gas concentration level amount. A calibration log may be received from the VOC detector. The calibration log may comprise an identifier of the VOC detector, the gas concentration level amount, and a date indicating when the VOC detector received the gas concentration level amount and the gas according to the gas concentration level amount.

25 Claims, 4 Drawing Sheets

U.S. PATENT DOCUMENTS

2006/0020186 A1* 1/2006 Brister et al. ............... 600/345
2007/0000310 A1* 1/2007 Yamartino et al. ........... 73/40.7
2008/0120043 A1 5/2008 Miller et al.

OTHER PUBLICATIONS

"2nd Annual Fugitive Emissions—Leak Detection and Repair Symposium"; ISA Technical Conference Brochure; Nov. 2002.

"Introducing the Allegro CX(TM) Field Computer"; Product Newswire (product announcement); Jun. 21, 2004.

"New from Accutech, Wireless Acoustic Monitor Field Units Make Fugitive Emissions Monitoring Compliance Easy"; Product Announcement/Description; Feb. 10, 2004.

"LDARManager™ Makes Fugitive Emission Monitoring a Breeze TISCOR launches its newest product for Leak Detection and Repair"; product announcement/description; Nov. 8, 2002.

* cited by examiner

CALIBRATION MANAGEMENT FOR VOLATILE ORGANIC COMPOUND DETECTOR

RELATED APPLICATIONS

This application claims priority to U.S. Provisional Patent Application No. 60/890,396, filed Feb. 16, 2007, titled CALIBRATION OF VOLATILE ORGANIC COMPOUND DETECTOR, and the entire disclosure of which is herein incorporated by reference.

BACKGROUND

1. Field of the Invention

Implementations of various technologies described herein are directed to volatile organic compound (VOC) detection and to various methods and/or systems for managing the calibration of VOC detectors.

2. Description of the Related Art

The following descriptions and examples do not constitute an admission as prior art by virtue of their inclusion within this section.

Industrial plants that handle volatile organic compounds (VOCs) sometimes experience unwanted emissions of those compounds into the atmosphere from point sources, such as smokestacks, and non-point sources, such as valves, pumps, and/or vessels containing the VOCs. Emissions from non-point sources typically occur due to leakage of the VOCs from joints and/or seals and may be referred to herein as "fugitive emissions". Fugitive emissions from control valves typically occur as leakage through the packing set around the valve stem. Control valves used in demanding service conditions involving large temperature fluctuations and frequent movements of the valve stem commonly suffer accelerated deterioration of the valve stem packing set.

The United States Environmental Protection Agency (EPA) has promulgated regulations specifying maximum permitted leakage of certain hazardous air pollutants, such as benzene, toluene, 1,1,1-trichloroethane, from certain hardware or fixtures, e.g., control valves. Fugitive emissions are typically monitored using a VOC detector, which may also be referred to as a vapor analyzer. Government regulations require that VOC detectors used in the testing of valves and other components in petrochemical processing or manufacturing facilities be calibrated at various intervals. These calibration activities must be documented and records made available for inspection for up to five years. If the calibrations are not performed, or if they are performed but not documented, the facility owner can be fined and/or suffer other regulatory sanctions.

SUMMARY

Described herein are implementations of various technologies for managing the calibration of a VOC detector. In one implementation, an initiation request may be received indicating a gas concentration level amount to be used for calibrating a VOC detector. A gas may be provided to the VOC detector according to the gas concentration level amount. The VOC detector may be provided with the gas concentration level amount. A calibration log may be received from the VOC detector. The calibration log may comprise an identifier of the VOC detector, the gas concentration level amount, and a date indicating when the VOC detector received the gas concentration level amount and the gas according to the gas concentration level amount.

In another implementation, a validation request may be received indicating a gas concentration level amount. Gas may be provided to the VOC detector according to the gas concentration level amount. A detection message indicating a concentration level of gas detected by the VOC detector may be received. The calibration of the VOC detector may be validated based on the gas concentration level amount and the concentration level of gas detected by the VOC detector.

The above referenced summary section is provided to introduce a selection of concepts in a simplified form that are further described below in the detailed description section. The summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

Implementations of various technologies will hereafter be described with reference to the accompanying drawings. It should be understood, however, that the accompanying drawings illustrate only the various implementations described herein and are not meant to limit the scope of various technologies described herein.

DETAILED DESCRIPTION

The discussion below is directed to certain specific implementations. It is to be understood that the discussion below is only for the purpose of enabling a person with ordinary skill in the art to make and use any subject matter defined now or later by the patent "claims" found in any issued patent herein.

The following paragraphs generally describe one or more implementations of various techniques directed to calibrating a volatile organic compound (VOC) detector. In one implementation, the VOC detector calibration system includes a VOC detector and a spanbox in communication with a personal digital assistant (PDA).

In operation, a user selects the VOC detectors to be calibrated from a list of available VOC detectors presented on the PDA. The user may further select a set of gas-cylinders to be used in the calibration according to a 4-point set of qualifying criteria. The VOC detectors may then be calibrated according to device-specific calibration methods.

In general, calibration involves providing gas with a specific methane level into the VOC detectors, and identifying the specific level to the VOC detector. The spanbox provides the gas containing the specific methane level from cylinders connected to the spanbox, to the VOC detectors.

After calibration, the VOC detectors may be checked to ensure proper detection. Again, the spanbox provides the gas with specific methane level into the VOC detectors. The VOC detectors determine the methane content of the gas, and signal the detected methane level to the PDA. The software on the PDA compares the detected level to the actual level and determines whether the VOC detectors pass the validation.

Validation may be based on the accuracy within which the VOC detectors detect the actual methane levels. Further, the validation may be based on an average of detected methane levels over several trials. Alternately, the validation may be based on how much time it takes for the VOC detectors to detect the actual level of methane in the gas. One or more implementations of various techniques for calibrating a VOC detector and validating the calibration of the VOC detector will now be described in more detail with reference to FIGS. 1-5 in the following paragraphs.

Figure 1:
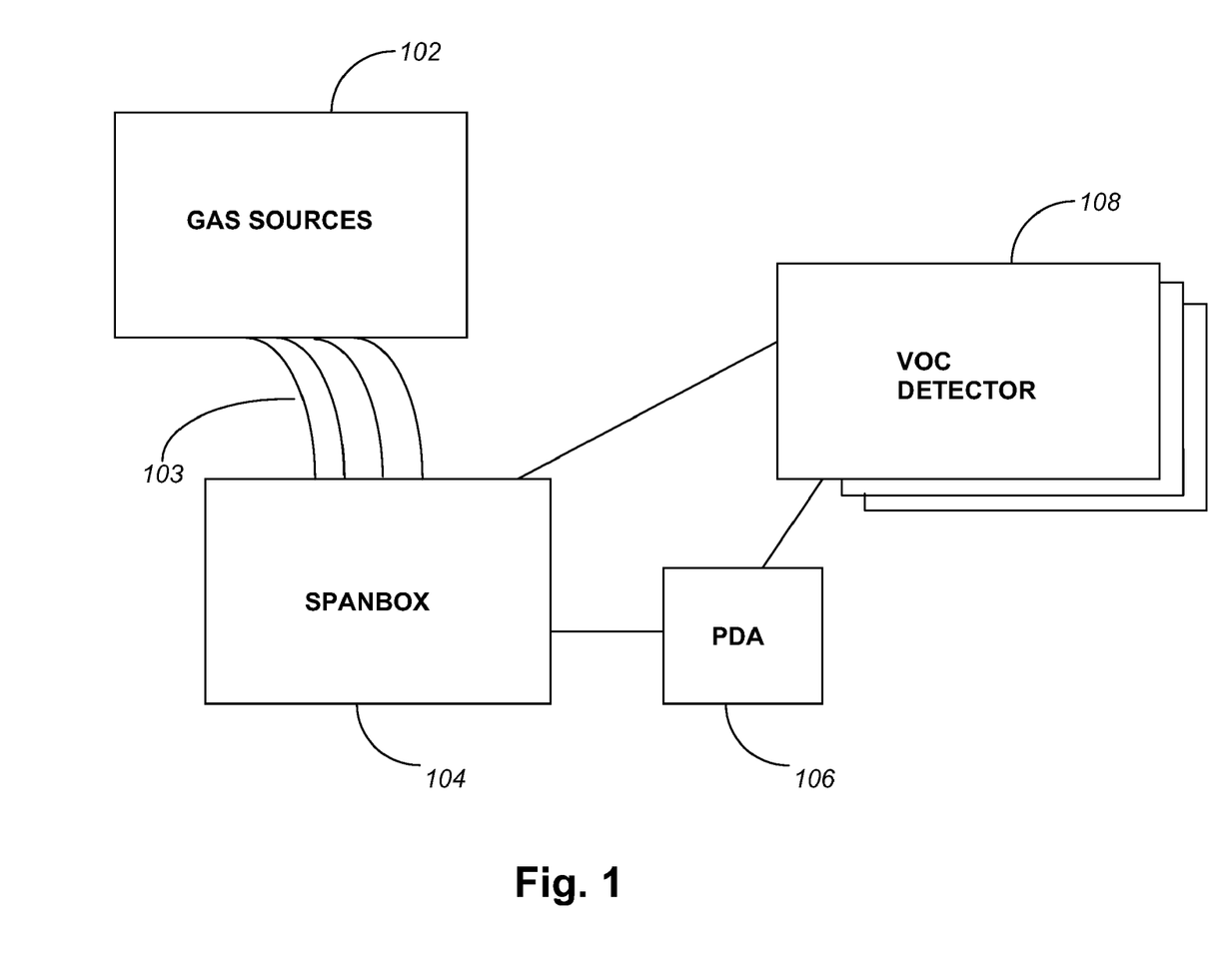
FIG. 1 illustrates a schematic diagram of a VOC detector calibration system in accordance with one or more implementations of various technologies described herein.

FIG. 1 illustrates a block diagram of a VOC detector calibration system 100 in accordance with one or more implementations of various technologies described herein. The calibration system 100 may include one or more gas sources 102, a spanbox 104, a PDA 106, and one or more VOC detectors 108.

The gas sources 102 may be configured to provide gas to the calibration system 100. The gas sources 102 may provide different concentrations of gas over each of the gas lines 103 to the spanbox 104. For example, the gas sources 102 may provide a methane gas concentration of 100 parts-per-million (PPM) over a first gas line, a concentration of 550 PPM over a second gas line, 750 PPM over a third gas line, etc.

The spanbox 104 may be configured to facilitate the delivery of gas to the VOC detector 108. The gas sources 102 may be coupled to the spanbox 104 via one or more gas lines 103. In one implementation, each gas line 103 may provide a different concentration of methane gas to the spanbox 104. Accordingly, the spanbox 104 may select a specific gas concentration from among the gas lines 103, and provide the selected gas concentration to the VOC detectors 108. Although various implementations described herein are with reference to methane gas, it should be understood that in some implementations, other types of gas may be used, such as hexane, propane, carbon tetrachloride, and the like.

Further, although various implementations are described with reference to a spanbox 104 providing gas to the VOC detector 108, it should be understood that in some implementations, the gas may be delivered directly to the VOC detector 108 without use of a spanbox 104. For example, the delivery of the gas to the VOC detector 108 may be performed manually, using bags, containers, and the like.

Figure 2:
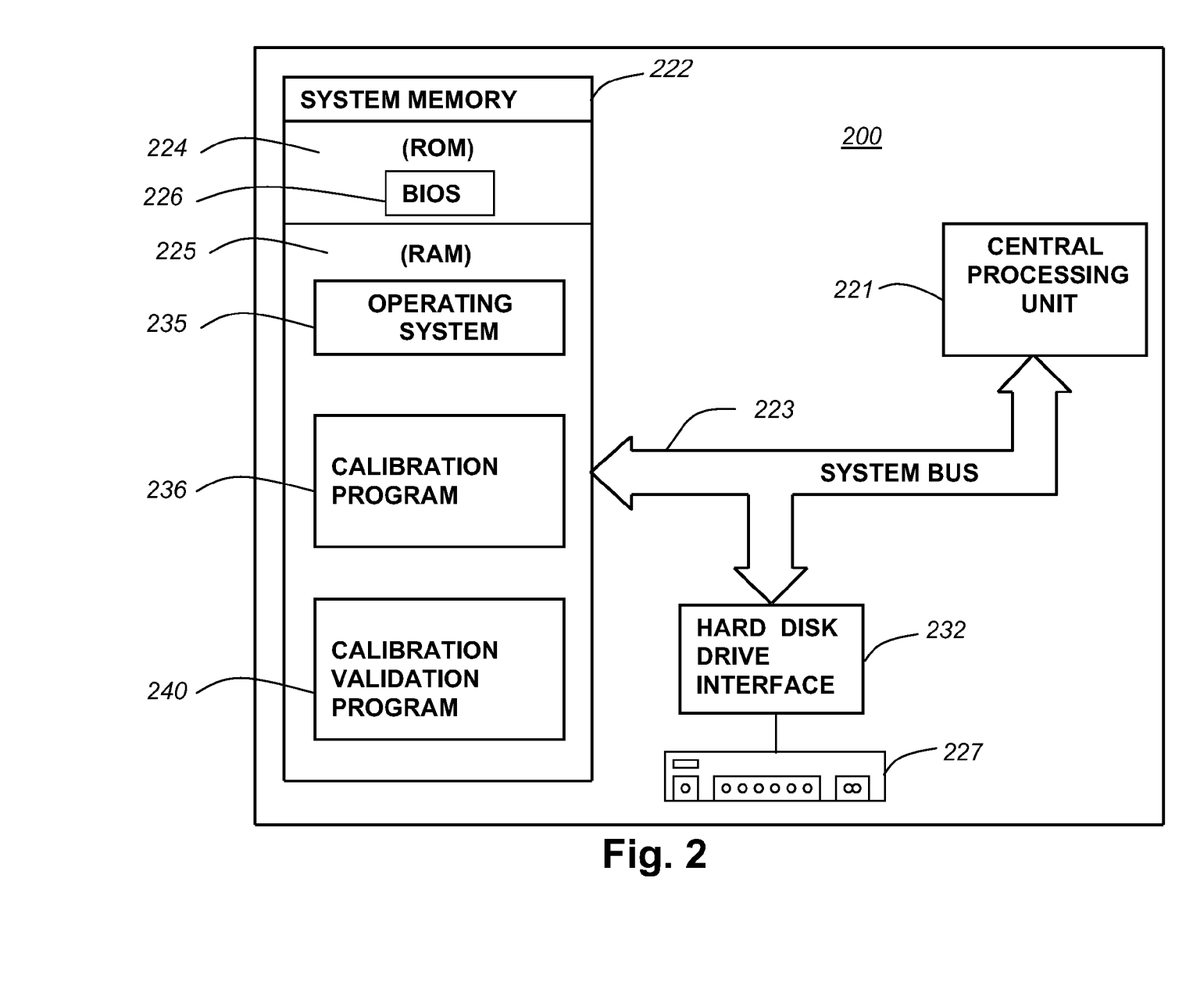
FIG. 2 illustrates a schematic diagram of a personal digital assistant (PDA) in accordance with one or more implementations of various technologies described herein.

The spanbox 104 may be in communication with the PDA 106, which is described in more detail in FIG. 2. The spanbox 104 may also be coupled to the VOC detectors 108. The PDA 106 may be in communication with the spanbox 104 and the VOC detectors 108. Communication between the PDA 106 and the spanbox 104 or the VOC detectors 108 may occur over wired or wireless connections. In one implementation, the PDA 106 communicates with the spanbox 104 over a serial cable, and with the VOC detector 108 via Bluetooth communications.

The VOC detectors 108 may be configured to detect volatile organic chemicals, emissions gases, nitro-aromatics, chemical warfare agents and the like. In one implementation, the VOC detectors 108 are TVA-1000's available from The Foxboro Company of Massachusetts, USA. However, it should be understood that some implementations may use other types of VOC detectors.

FIG. 2 illustrates a schematic diagram of a PDA 200 in accordance with one or more implementations of various technologies described herein. The PDA 200 may include a central processing unit (CPU) 221, a system memory 222 and a system bus 223 that couples various system components including the system memory 222 to the CPU 221. Although only one CPU is illustrated in FIG. 2, it should be understood that in some implementations the PDA 200 may include more than one CPU. The system bus 223 may be any of several types of bus structures, including a memory bus or memory controller, a peripheral bus, and a local bus using any of a variety of bus architectures. By way of example, and not limitation, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. The system memory 222 may include a read only memory (ROM) 224 and a random access memory (RAM) 225. A basic input/output system (BIOS) 226, containing the basic routines that help transfer information between elements within the PDA 200, such as during start-up, may be stored in the ROM 224.

The PDA 200 may further include a hard disk drive 227 for reading from and writing to a hard disk. The hard disk drive 227 may be connected to the system bus 223 by a hard disk drive interface 232. The drives and their associated computer-readable media may provide nonvolatile storage of computer-readable instructions, data structures, program modules and other data for the PDA 200.

The PDA 200 may further include computer-readable media that may be accessed by the CPU 221. For example, such computer-readable media may include computer storage media and communication media. Computer storage media may include volatile and non-volatile, and removable and non-removable media implemented in any method or technology for storage of information, such as computer-readable instructions, data structures, program modules or other data. Computer storage media may further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium which can be used to store the desired information and which can be accessed by the CPU 221.

Communication media may embody computer readable instructions, data structures, program modules or other data in a modulated data signal, such as a carrier wave or other transport mechanism and may include any information delivery media. The term "modulated data signal" may mean a signal that has one or more of its characteristics set or changed in such a manner as to encode information in the signal. By way of example, and not limitation, communication media may include wired media such as a wired network or direct-wired connection, and wireless media such as acoustic, RF, infrared and other wireless media. Combinations of any of the above may also be included within the scope of computer readable media.

A number of program modules may be stored on ROM 224 or RAM 225, including an operating system 235, a calibration program 236 and a calibration validation program 240. The operating system 235 may be any suitable operating system that may control the operation of a networked personal or server computer, such as Windows® XP, Mac OS® X, Unix-variants (e.g., Linux® and BSD®), and the like. The calibration program 236 will be described in more detail with reference to FIG. 3 in the paragraphs below. Similarly, the calibration validation program 240 will be described in more detail with reference to FIG. 4 in the paragraphs below.

It should be understood that the various technologies described herein may be implemented in connection with hardware, software or a combination of both. Thus, various technologies, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the various technologies. In the case of program code execution on programmable computers, the computing device may include a processor, a storage medium readable by the processor (including volatile and non-volatile memory and/or storage elements), at least one input device, and at least one output device. One or more programs that may implement or utilize the various technologies described herein may use an application programming interface (API), reusable controls, and the like. Such programs may be implemented in a high level procedural or object oriented programming language to communicate with a computer system. However, the program(s) may be implemented in assembly or machine language, if desired. In any case, the language may be a compiled or interpreted language, and combined with hardware implementations.

For example, the various technologies described herein may be implemented in distributed computing environments where tasks are performed by remote processing devices that are linked through a communications network, e.g., by hard-wired links, wireless links, or combinations thereof. In a distributed computing environment, program modules may be located in both local and remote computer storage media including memory storage devices.

Figure 3:
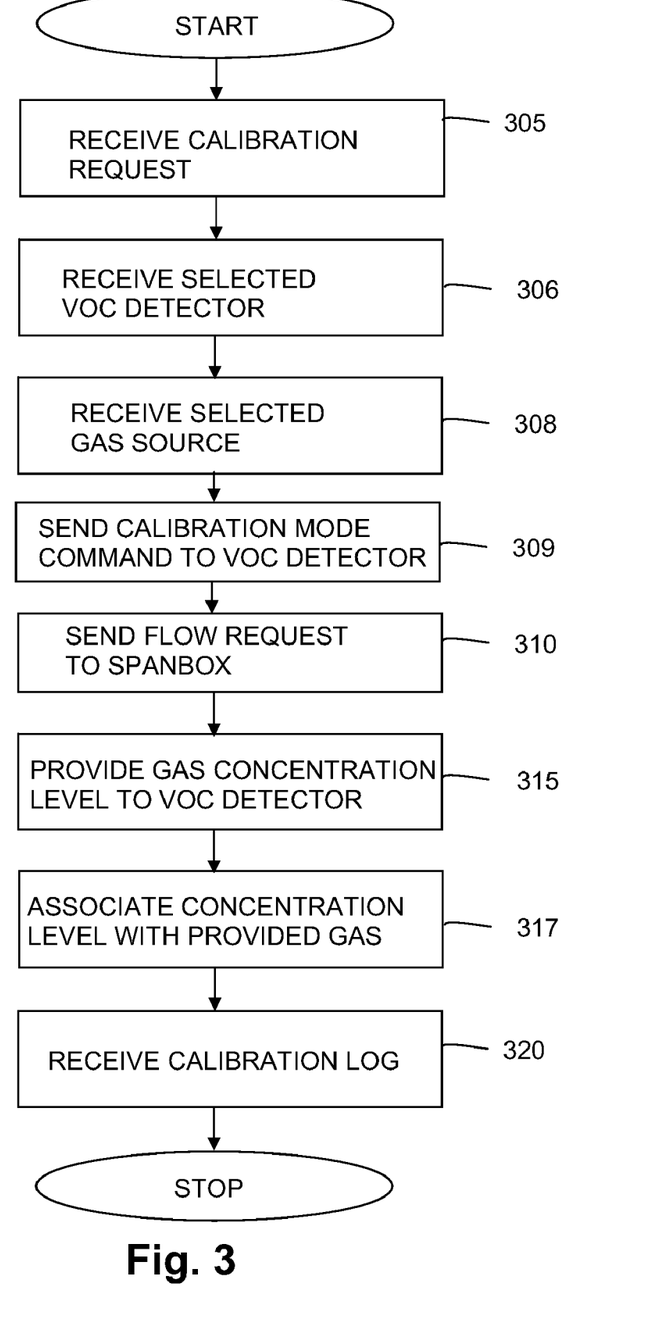
FIG. 3 illustrates a flow diagram of a method for calibrating a VOC detector in accordance with implementations of various technologies and techniques described herein.

FIG. 3 illustrates a flow diagram of a method 300 for calibrating a VOC detector in accordance with implementations of various technologies and techniques described herein. It should be understood that while the flow diagram indicates a particular order of execution of the operations, in some implementations, the operations might be executed in a different order. In one implementation, the method 300 may be performed by the calibration program 236.

Before validation, the VOC detector 108 may need to be warmed up for a pre-determined time period. In one implementation, the calibration program 236 may measure the amount of time in the warm-up period and store the time. A determination may be made as to whether the warm-up period is sufficient for the VOC detector 108. For example, if the warm-up period is equal to or greater than a pre-determined amount of time, e.g., 30 minutes, the VOC detector 108 may be deemed as having passed. Alternatively, if the warm-up period is less than the predetermined amount, then the VOC detector may be deemed as having failed.

At step 305, a calibration request may be received by the PDA 106. In one implementation, the calibration request may be a request from a user operating the PDA 106. The calibration request may specify a gas concentration level to be used for calibrating the VOC detector 108.

At step 306, a VOC detector selection may be received by the PDA 106. In one implementation, the calibration program 236 may be configured to present a list of VOC detectors 108 that are available for calibration. Accordingly, a user operating the PDA 106 may select one of the VOC detectors 108 to be calibrated.

At step 308, a gas source 102 selection may be received by the PDA 106. In one implementation, the calibration program 236 may be configured to present a list of gas sources 102 that are available for calibration. Accordingly, a user operating the PDA 106 may select one or more of the gas sources 102 to provide the gas for calibrating the VOC detector selected at step 306.

At step 309, a calibration mode command may be sent to the VOC detector 108. In response to the command, the VOC detector 108 may be configured to send a calibration log to the PDA 106 after the calibration is complete.

At step 310, a flow request may be sent to the spanbox 104. The flow request may include the gas concentration level amount specified in the calibration request received in step 305. In response, the spanbox 104 may provide a gas with the specified gas concentration level to the VOC detector 108.

At step 315, the calibration program 236 may provide the VOC detector 108 with the gas concentration level amount. In one implementation, the VOC detector 108 may combust the gas provided by the spanbox 104 to derive an electronic signature. At step 317, the VOC detector 108 may internally store a record that associates the electronic signature of the combusted gas with the gas concentration level amount. At step 320, a calibration log may be received from the VOC detector 108 by the calibration program 236 that includes an identifier of the VOC detector 108, e.g., a serial number, the gas concentration level amount, and a date and or time that the calibration takes place. The calibration log may be stored on the PDA 106 or another device. Advantageously, by storing the calibration log digitally, typical recordation errors that may otherwise incur regulatory sanctions can be avoided.

In one implementation, one or more VOC detectors 108 may be selected at step 306 and steps 310-320 may be repeated for each selected VOC detector. Further, calibrating a VOC detector typically requires multiple gas concentration level specifications. As such, steps 310-320 may be repeated for each gas concentration level specification on each VOC detector 108 selected at step 306.

Figure 4:
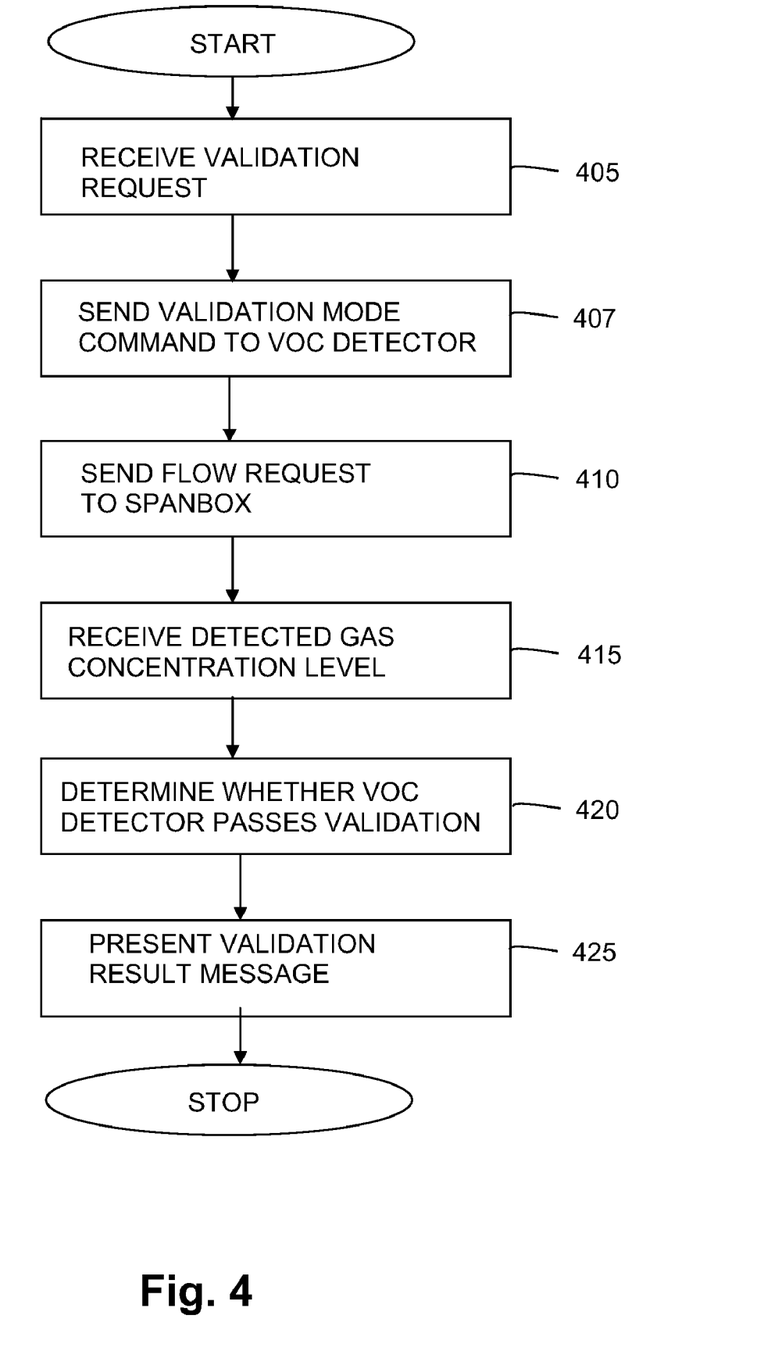
FIG. 4 illustrates a flow diagram of a method for validating the calibration of a VOC detector in accordance with implementations of various technologies and techniques described herein.

FIG. 4 illustrates a flow diagram of a method 400 for validating the calibration of a VOC detector 108 in accordance with implementations of various technologies and techniques described herein. It should be understood that while the flow diagram indicates a particular order of execution of the operations, in some implementations, the operations might be executed in a different order. In one implementation, the method 400 may be performed by the calibration validation program 240.

At step 405, a validation request may be received by the PDA 106. In one implementation, the validation request may be a request from a user operating the PDA 106. The validation request may specify a gas concentration level to be used for validating the calibration of the VOC detector 108.

At step 407, a validation mode command may be sent to the VOC detector 108. In response to receiving the command, the VOC detector 108 may be configured to analyze the gas concentration level and send the detected gas concentration level to the PDA 106.

At step 410, a flow request may be sent to the spanbox 104. The flow request may include the gas concentration level amount specified in the validation request received in step 405. In response to receiving the flow request, the spanbox 104 may provide a gas with the specified gas concentration level to the VOC detector 108.

In one implementation, the VOC detector 108 operating in the validation mode may analyze the gas provided by the spanbox 104, and send a signal specifying the concentration of gas detected to the PDA 106. At step 415, the PDA 106 may receive a detection message indicating the concentration level of gas detected by the VOC detector 108. In one implementation, the validation program 240 may be configured to measure the amount of time it would take the VOC detector 108 to detect a gas concentration level within a specified range of the actual gas concentration level.

At step 420, the validation program 240 may determine whether the VOC detector 108 passes the validation test. In one implementation, determining whether the VOC detector 108 passes the validation test may be based on whether the detected gas concentration level is within a specified range of the actual gas concentration level. In another implementation, determining whether the VOC detector passes the validation test may be based on whether gas concentration level detected by the VOC detector is within a specified range of the gas concentration level amount within a specified time period. The specified range, the specified percentage and/or the specified time periods may be user specified. For example, the specified percentage may be 90 percent. In one implementation, the VOC detector 108 may be calibrated and validated three times and an average of the variance between the detected gas concentration level is calculated. In this implementation, the validation test may be based on whether the detected gas concentration level is within a specified percentage of a known gas.

At step 425, the validation program 240 may present a validation result message. If the VOC detector 108 passes the validation test, the validation program 240 may present a validation success message. If the VOC detector 108 does not pass the validation test, the validation program 240 may present a validation failure message.

In one implementation, the validation program 240 may store the result of the validation test. The stored result may also include an identifier of the VOC detector 108 validated, the concentration level of the gas provided for the validation test, and a date and/or time of the validation.

Although implementations of various technologies described herein are described with reference to a PDA, it should be understood that some implementations may be operational with other types of computing systems, such as laptop devices, personal computers, multi-processor systems, microprocessor-based systems, programmable consumer electronics, minicomputers, and the like.

While the foregoing is directed to implementations of various technologies described herein, other and further implementations may be devised without departing from the basic scope thereof, which may be determined by the claims that follow. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for calibrating a volatile organic compound (VOC) detector, comprising:
   receiving an initiation request indicating a gas concentration level amount to be used for calibrating a VOC detector, wherein the VOC detector is configured to test whether valves and other components in petrochemical facilities are leaking;
   providing gas according to the gas concentration level amount to the VOC detector;
   providing the VOC detector with the gas concentration level amount via a wireless connection; and
   receiving a calibration log from the VOC detector via the wireless connection, wherein the calibration log comprises an identifier of the VOC detector, the gas concentration level amount, an electronic signature of the provided gas, a date indicating when the VOC detector received the gas concentration level amount and the gas according to the gas concentration level amount, wherein the electronic signature is derived by combusting the provided gas.

2. The method of claim 1, further comprising associating the electronic signature with the gas concentration level amount.

3. The method of claim 1, further comprising:
   presenting a list of available VOC detectors; and
   receiving a selection for the VOC detector.

4. The method of claim 1, further comprising sending a flow request to a spanbox to provide gas to the VOC detector.

5. The method of claim 4, further comprising:
   presenting a list of available gas sources;
   receiving a selection for one or more gas sources, wherein the spanbox provides gas from one of the selected gas sources.

6. The method of claim 1, further comprising:
   receiving a validation request indicating the gas concentration level amount used for calibrating the VOC detector;
   providing gas according to the gas concentration level amount to the VOC detector;
   receiving a detection message indicating the concentration level of gas detected by the VOC detector; and
   validating the calibration of the VOC detector based on the gas concentration level amount and the concentration level of gas detected by the VOC detector.

7. The method of claim 6, wherein validating the calibration of the VOC detector comprises determining whether the VOC detector passes a validation test based on the detected concentration level of gas, and the gas concentration level amount.

8. The method of claim 7, further comprising displaying a message indicating whether the VOC detector passes the validation test.

9. The method of claim 6, wherein validating the calibration of the VOC detector comprises determining whether the detected concentration level is within a specified percentage of the gas concentration level amount.

10. The method of claim 6, wherein validating the calibration of the VOC detector comprises determining whether the detected concentration level is within a specified range of the gas concentration level amount and that the VOC detector detects the detected concentration level within a specified time period.

11. The method of claim 6, further comprising storing a validation record indicating an identifier of the VOC detector, a result indicating whether the VOC detector passes the validation test, and a date indicating when the VOC detector is validated.

12. The method of claim 6 wherein the gas concentration level is based on the electronic signature of the provided gas.

13. The method of claim 1, wherein the initiation request is received by a Personal Digital Assistant (PDA).

14. The method of claim 13, wherein the gas concentration level is provided by the PDA.

15. The method of claim 1, wherein the gas is provided by a spanbox.

16. A method for validating a calibration of a volatile organic compound detector (VOC detector), comprising:
   receiving a validation request indicating a gas concentration level amount;
   providing gas according to the gas concentration level amount to the VOC detector, wherein the VOC detector is configured to test whether valves and other components in petrochemical facilities are leaking;

receiving a detection message indicating a concentration level of gas detected by the VOC detector via a wireless connection, wherein the detected gas concentration level is based on an electronic signature of the provided gas, and wherein the electronic signature is derived by combusting the provided gas; and validating the calibration of the VOC detector based on the gas concentration level amount and the concentration level of gas detected by the VOC detector.

17. The method of claim 16, wherein validating the calibration of the VOC detector comprises determining whether the VOC detector passes a validation test based on whether the detected gas concentration level is within a specified percentage of the actual gas concentration level.

18. The method of claim 17, further comprising displaying a message indicating whether the VOC detector passes the validation test.

19. The method of claim 16, wherein validating the calibration of the VOC detector comprises determining whether the detected concentration level is within a specified percentage of the gas concentration level amount.

20. The method of claim 16, wherein validating the calibration of the VOC detector comprises determining whether the detected concentration level is within a specified range of the gas concentration level amount and that the VOC detector detects the detected concentration level within a specified time period.

21. The method of claim 16, further comprising storing a validation record indicating an identifier of the VOC detector, a result indicating whether the VOC detector passes the validation test, and a date indicating when the VOC detector is validated.

22. A system for calibrating a volatile organic compound (VOC) detector, comprising:

a processor; and a memory having stored thereon computer-executable instructions which, when executed by a computer, cause the computer to:

receive an initiation request indicating a gas concentration level amount to be used for calibrating a VOC detector, wherein the VOC detector is configured to test whether valves and other components in petrochemical facilities are leaking;

provide gas according to the gas concentration level amount to the VOC detector;

provide the VOC detector with the gas concentration level amount via a wireless connection; and receive a calibration log from the VOC detector via the wireless connection, wherein the calibration log comprises an identifier of the VOC detector, the gas concentration level amount, an electronic signature of the provided gas and a date indicating when the VOC detector is calibrated with the gas concentration level amount, wherein the electronic signature is derived by combusting the provided gas.

23. The system of claim 22, wherein the memory further comprises computer-executable instructions which, when executed by a computer, cause the computer to:

associate the electronic signature with the gas concentration level amount.

24. The system of claim 22, wherein the memory further comprises computer-executable instructions which, when executed by a computer, cause the computer to:

receive a validation request indicating the gas concentration level amount used for calibrating the VOC detector;

provide gas according to the gas concentration level amount to the VOC detector;

receive a detection message indicating the concentration level of gas detected by the VOC detector;

validate the calibration of the VOC detector based on the gas concentration level amount and the concentration level of gas detected by the VOC detector; and display a message indicating whether the VOC detector passes the validation test.

25. The system of claim 24 wherein the gas concentration level is based on the electronic signature of the provided gas.

* * * * *